United States Patent [19]

Myers et al.

[11] Patent Number: 5,567,439

[45] Date of Patent: Oct. 22, 1996

[54] DELIVERY OF CONTROLLED-RELEASE SYSTEMS(S)

[75] Inventors: Garry L. Myers; Gerald E. Battist, both of Reston; Richard C. Fuisz, Great Falls, all of Va.

[73] Assignee: Fuisz Technologies Ltd., Chantilly, Va.

[21] Appl. No.: 334,729

[22] Filed: Nov. 4, 1994

Related U.S. Application Data

[63] Continuation-in-part of Ser. No. 259,496, Jun. 14, 1994, and Ser. No. 259,258, Jun. 14, 1994.

[51] Int. Cl.$^6$ ............................... A61K 9/20; A61K 9/22
[52] U.S. Cl. ..................... 424/486; 424/464; 424/468; 424/479; 424/488; 424/439; 424/440
[58] Field of Search .................................. 424/464, 468, 424/479, 488, 439, 440

[56] References Cited

U.S. PATENT DOCUMENTS

| | | | |
|---|---|---|---|
| 2,826,169 | 3/1958 | Le Veen | 54/79.4 |
| 2,918,404 | 12/1959 | Mende et al. | 514/683 |
| 3,019,745 | 2/1962 | Du Bois et al. | 425/9 |
| 3,036,532 | 5/1962 | Bowe | 425/9 |
| 3,067,743 | 12/1962 | Merton et al. | 424/431 |
| 3,070,045 | 12/1962 | Bowe | 425/9 |
| 3,073,262 | 1/1963 | Bowe | 425/9 |
| 3,095,258 | 6/1963 | Scott | 264/177.14 |
| 3,118,396 | 1/1964 | Brown et al. | 425/9 |
| 3,131,428 | 5/1964 | Mika | 264/177.13 |
| 3,308,221 | 3/1967 | Opfell | 264/168 |
| 3,324,061 | 6/1967 | Tanquary et al. | 264/177.13 |
| 3,482,998 | 12/1969 | Carroll et al. | 426/646 |
| 3,523,889 | 8/1970 | Eis | 210/713 |
| 3,557,717 | 1/1971 | Chivers | 426/660 |
| 3,595,675 | 7/1971 | Ash et al. | 426/576 |
| 3,615,671 | 10/1971 | Schoaf | 426/96 |
| 3,625,214 | 12/1971 | Higuchi | 424/424 |
| 3,676,148 | 7/1972 | De Weese et al. | 426/576 |
| 3,723,134 | 3/1973 | Chivers | 426/660 |
| 3,762,846 | 10/1973 | Chivers | 425/7 |
| 3,766,165 | 10/1973 | Rennhard | 536/123.1 |
| 3,856,443 | 12/1974 | Salvi | 425/9 |
| 3,875,300 | 4/1975 | Homm et al. | 424/433 |
| 3,876,794 | 4/1975 | Rennhard | 426/548 |
| 3,925,525 | 12/1975 | La Nieve | 264/207 |
| 3,930,043 | 12/1975 | Warning et al. | 426/515 |
| 3,951,821 | 4/1976 | Davidson | 252/1 |
| 3,967,623 | 7/1976 | Butterworth et al. | 604/370 |
| 3,972,725 | 8/1976 | Nicol | 127/58 |
| 3,981,739 | 9/1976 | Dmitrovsky et al. | 127/60 |
| 3,992,265 | 11/1976 | Hansen | 435/288.5 |
| 4,056,364 | 11/1977 | Dmitrovsky et al. | 422/253 |
| 4,086,418 | 4/1978 | Turbak et al. | 536/30 |
| 4,090,920 | 5/1978 | Studer, Jr. | 435/288.4 |
| 4,136,145 | 1/1979 | Fuchs et al. | 264/164 |
| 4,153,512 | 5/1979 | Messner et al. | 435/33 |
| 4,159,210 | 6/1979 | Chen et al. | 127/29 |
| 4,293,570 | 10/1981 | Vadasz | 426/3 |
| 4,303,684 | 12/1981 | Pitchon et al. | 426/312 |
| 4,338,350 | 7/1982 | Chen et al. | 426/658 |
| 4,348,420 | 9/1982 | Lynch et al. | 426/272 |
| 4,362,757 | 12/1982 | Chen et al. | 426/599 |
| 4,371,516 | 2/1983 | Gregory et al. | 424/485 |
| 4,376,743 | 3/1983 | Dees | 264/103 |
| 4,492,685 | 1/1985 | Keith et al. | 424/78.06 |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0287488A1 | 3/1988 | European Pat. Off. . |
| 0387950A1 | 8/1990 | European Pat. Off. . |
| 86052 | 4/1988 | Israel . |
| 86053 | 4/1988 | Israel . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 519858 | 5/1971 | Switzerland . |
| 489211 | 7/1986 | Switzerland . |
| 2155934 | 3/1985 | United Kingdom . |
| WO91/18613 | 5/1991 | WIPO . |

OTHER PUBLICATIONS

R. H. Doremus, "Crystallization of Sucrose From Aqueous Solution," *Journal of Colloid and Interface Science*, 104, pp. 114–120 (1985).

P. Bennema, "Surface Diffusion and the Growth of Sucrose Crystals," *Journal of Crystal Growth*, 3,4 pp. 331–334 (1968).

T. D. Simpson, et al., "Crystalline Forms of Lactose Produced in Acidic Alcoholic Media," *Journal of food Science*, 47, pp. 1948–1954 (1982).

A. D. Randolph, et al., "Continuous Sucrose Nucleation," *The Internationl Sugar Journal*, pp. 8–12 (1974).

K. B. Domovs, et al., "Methanol–Soluble Complexes of Lactose and of other Carbohydrates," *J. Dairy Science*, 43, pp. 1216–1223 (1960).

A. D. Randolph, et al., "Continuous Sucrose Nucleation," *The International Sugar Journal*, pp. 35–38 (1974).

A. D. Randolph, et al., "Continuous Sucrose Nucleation," *The International Sugar Journal*, pp. 73–77 (1974).

ICI Americas Inc., "ICI Americas Products for Cosmetics and Pharmaceuticals," (1977).

Domino Sugar Corporation, "Co–crystallization".

Domino Sugar Corporation, "Raspberry".

Domino Sugar Corporation, "Molasses Dark".

*Primary Examiner*—Amy Hulina
*Attorney, Agent, or Firm*—Hoffmann & Baron

[57] ABSTRACT

The present invention is a method and a dosage unit for delivery of a controlled-release system. The dosage unit is a quick dissolve unit which can be prepared by mixing uncured shearform matrix and a controlled-release system, either molding or compacting a unit dosage form and curing the shearform matrix. The controlled-release systems used in the present invention include instantaneous release components, delayed release components, sustained release components, and combinations thereof.

11 Claims, No Drawings

U.S. PATENT DOCUMENTS

| | | | |
|---|---|---|---|
| 4,496,592 | 1/1985 | Kuwahara et al. | 426/5 |
| 4,500,546 | 2/1985 | Turbak et al. | 514/781 |
| 4,511,584 | 4/1985 | Perel et al. | 426/99 |
| 4,526,525 | 7/1985 | Oiso et al. | 425/9 |
| 4,585,797 | 4/1986 | Cioca | 514/773 |
| 4,619,833 | 10/1986 | Anderson | 426/548 |
| 4,772,477 | 9/1988 | Weiss et al. | 426/99 |
| 4,793,782 | 12/1988 | Sullivan | 425/7 |
| 4,855,326 | 8/1989 | Fuisz | 514/777 |
| 4,872,821 | 10/1989 | Weiss | 425/9 |
| 4,873,085 | 10/1989 | Fuisz | 424/400 |
| 4,879,108 | 11/1989 | Yang et al. | 424/440 |
| 4,885,281 | 12/1989 | Hanstein et al. | 514/53 |
| 4,978,537 | 12/1990 | Song | 426/5 |
| 4,997,856 | 3/1991 | Fuisz | 514/777 |
| 5,011,532 | 4/1991 | Fuisz | 106/215 |
| 5,028,632 | 7/1991 | Fuisz | 514/772 |
| 5,034,421 | 7/1991 | Fuisz | 514/772 |
| 5,073,387 | 12/1991 | Whistler | 426/7 |
| 5,082,682 | 1/1992 | Peterson | 426/564 |
| 5,082,684 | 1/1992 | Fung | 426/602 |
| 5,084,295 | 1/1992 | Whelan et al. | 426/565 |
| 5,089,606 | 2/1992 | Cole et al. | 536/54 |
| 5,094,872 | 3/1992 | Furcsik et al. | 426/578 |
| 5,096,492 | 3/1992 | Fuisz | 106/215 |
| 5,236,734 | 8/1993 | Fuisz | 426/641 |
| 5,348,758 | 9/1994 | Fuisz et al. | 426/660 |
| 5,380,473 | 1/1995 | Bogue et al. | 264/11 |
| 5,429,836 | 7/1995 | Fuisz | 426/601 |
| 5,456,932 | 10/1995 | Fuisz et al. | 426/548 | ically
DELIVERY OF CONTROLLED-RELEASE SYSTEMS(S)

This application is a continuation-in-part application of U.S. application Ser. No. 08/259,496, pending and U.S. application Ser. No. 08/259,258, pending, both of which were filed Jun. 14, 1994. The contents of both patent applications are incorporated herein by reference.

BACKGROUND OF THE INVENTION

The present invention relates to controlled release systems, and, in particular to improved delivery of controlled release system or systems.

The convenience of administering a single dose of a medication which releases active ingredients in a controlled fashion over an extended period of time, as opposed to the administration of a number of single doses at regular intervals, has long been recognized in the pharmaceutical arts. The advantage to the patient and clinician in having consistent and uniform blood levels of medication over an extended period of time are likewise recognized. The advantages of a variety of controlled-release dosage forms are well known. Among the most important advantages are: (1) increased contact time for the drug to allow for local activity in the stomach, intestine or other locus of activity; (2) increased and more efficient absorption for drugs which have specific absorption sites; (3) the ability to reduce the number of dosages per period of time; (4) employment of less total drug; (5) minimization or elimination of local and/or systemic side effects; (6) minimization of drug accumulation associated with chronic dosing; (7) improved efficiency and safety of treatment; (8) reduced fluctuation of drug level; and (9) better patient compliance with overall disease management.

Additionally, many experts believe controlled release drug delivery has many important non-therapeutic ramifications as well, including a financial saving to the patient in terms of fewer lost work days, reduced hospitalization and fewer visits to the physician.

It is known that certain design parameters are critical to proper drug delivery. Typically, they are: (1) delivering the drug to the target tissue; (2) supplying the drug in the correct temporal pattern for a predetermined period of time; and (3) fabricating a delivery system that provides drug in the desired spatial and temporal pattern. Controlled release drug delivery systems are intended to utilize these parameters to achieve the aforementioned advantages when compared to conventional pharmaceutical dosing.

"Controlled-release" is used herein to describe a method and composition for making an active ingredient available to the biological system of a host. Controlled-release includes the use of instantaneous release, delayed release, and sustained release. "Instantaneous release" is self-explanatory in that it refers to immediate release to the biosystem of the host. "Delayed release" means the active ingredient is not made available to the host until some time delay after administration. (Dosages are usually administered by oral ingestion in the context of the present invention, although other forms of administration are not precluded from the scope of the present invention). "Sustained Release" generally refers to release of active ingredient whereby the level of active ingredient available to the host is maintained at some level over a period of time. The method of effecting each type of release can be varied. For example, the active-ingredient can be associated physically and/or chemically with a surfactant, a chelating agent, etc. Alternatively, the active ingredient can be masked by a coating, a laminate, etc. Regardless of the method of providing the desired release pattern, the present invention contemplates delivery of a controlled-release system which utilizes one or more of the "release" methods and compositions. Moreover, the present invention can be an element of the release method and/or composition, especially with respect to instantaneous release systems(s).

The patent and scientific literature is replete with various sustained release (SR) methods and formulations. For common methods of obtaining SR systems, see *Sustained and Controlled Release Drug Delivery Systems*, Robinson, Joseph R., Ed., PP 138–171, 1978, Marcel Dekker, Inc. New York, N.Y. For example, it is known to fill polymeric capsules with a solid, liquid, suspension or gel containing a therapeutic agent which is slowly released by diffusion through the capsule walls. Heterogeneous matrices, for example compressed tablets, control the release of their therapeutic agents either by diffusion, erosion of the matrix or a combination of both. Other SR systems focus on the fabrication of laminates of polymeric material and therapeutic agent which are then formed into a sandwich, relying on diffusion or erosion to control release of the therapeutic agent. Liquid-Liquid encapsulated in a viscous syrup-like solution of polymer, have also been known to be useful in controlling release of the therapeutic agent. Additionally, it is generally known that heterogeneous dispersions or solution of therapeutic agents in water-swellable hydrogel matrices are useful in controlling the release of the agent by slow surface-to-center swelling of the matrix and subsequent diffusion of the agent from the water-swollen part of the matrix.

During dissolution of a controlled-release matrix tablet, the dosage form generally remains as a non-disintegrating, slowly eroding entity from which the therapeutic agent leaches out, through a diffusion controlled process. Conventional SR formulations are generally designed to release their actives over an extended period of time, usually 8–24 hours. Conventional SR formulations use waxes or hydrophilic gums as the primary drug carriers to prolong the release of the active ingredients. In conventional wax matrix tablet formulations, the drug is dispersed in the wax matrix in the molten state. Conventional waxes and waxy materials used in pharmaceutical formulations are carnauba wax, spermaceti wax, candellila wax, cocoa butter, cetosteryl alcohol, beeswax, partially hydrogenated vegetable oils, ceresin, paraffin, myristyl alcohol, stearyl alcohol, cetylalcohol and stearic acid. They are generally used in amounts of about 10 to about 50% by weight of the total formulation.

Hydrophilic gums have also been known to be reasonably effective as SR carriers for both high-dose and low-dose drugs. Typical hydrophilic gums used as SR carrier materials are acacia, gelatin, tragacanth, veegum, xanthan gum, carboxymethyl cellulose (CMC), hydroxypropl methyl cellulose (HPMC), hydroxypropyl cellulose (HPC) and hydroxyethyl cellulose (HEC). Generally these materials are present in amounts of about 10 to 50% by weight of the final formulation.

Starch USP (potato or corn) is commonly used as a component in conventional tablet or hard shell capsule formulations. It generally functions in conventional applications as a diluent or as a disintegrant in oral dosage forms. Starch paste is also often used as a binder in these products. Various modified starches, such as carboxymethyl starch currently marketed under the trade name Explotab or Primojel are used both in tablets and capsules as disintegrating agents. The literature discloses that native and modified starches are useful in promoting rapid release of drugs from solid oral dosage forms. Additionally, native starch has been used in some instances as a binder to produce granulations of active drug substances. More recently, pregelatinized starch has been reported as being useful as an SR matrix for theophylline formulations by Herman and Remon, "Modified Starches as Hydrophilic Matrices for Controlled Oral Deliver; III Evaluation of Sustained-Release Theophylline Formulations Based on Thermal Modified Starch Matrices in Dogs," in *International Journal of Pharmaceutics*, 63 (1990) 201–205. In sustained release applications several types of modified starch were mixed with anhydrous theophylline (60:40 W/W) as well as with silicon dioxide (Aerosil 200) and sodium benzoate. In prior papers, (*International Journal of Pharmaceutics*, volumes 56 (1988) 145–153; 56 (1989) 51–63; and 56 (1989) 65–70) the authors discussed the use of both drum-drying and extrusion of native starches to obtain partial or full pregelatinization.

The existing sustained release technologies generally involve relatively complicated formulations and manufacturing processes which are difficult and expensive to precisely control. For example, one well known SR delivery system, OROS, marketed by the Alza Corporation, involves laser drilling through a tablet to create a passage for the release of the drug from the tablet core.

In all controlled release technologies it is desirable to be able to incorporate the active ingredient in its controlled-release pattern in a single dosage unit without deteriorating the active ingredient. Moreover, the dosage unit should be able to deliver the system without interfering with its release pattern.

Various methods have been devised to enable controlled-release systems to be delivered to a host without destruction of the delivery system during manufacturing, handling, and sales. For example, controlled-release systems have been provided in the form of beads or particles which are packaged in a gelatin capsule for oral dosage. This method of delivery of the controlled-release system prevents damage to the coating on the beads.

In many cases it may be desirable to provide an oral dosage form as a tablet. However, when controlled-release systems are incorporated in a chewable tablet, chewing of the tablet may often rupture the coatings on the active ingredient. This results in unpredictable release rates and delivery to the biosystem of the host. Moreover, when controlled-release components are incorporated in compression tablets, the extremely high pressure required to tablet can be expected to rupture the coatings. Consequently, the compression tablet form of delivery is not usable, or extremely tough elastic coatings are required to withstand normal tablet pressures.

Furthermore, when controlled-release active ingredients are incorporated in compression tablets, it may be difficult for many people to swallow such tablets. Furthermore, dissolution of high compression tablets is often small and erratic, resulting in localized hot spots of alimentary tract irritation where disintegration and release of the active ingredient finally occurs.

The present invention overcomes the disadvantages of the prior art by offering a simple and inexpensive means of incorporating a controlled-release system in a unit dosage form which avoids the shortcomings normally associated with unit dosage delivery systems.

SUMMARY OF THE INVENTION

In a first embodiment of the present invention a method of preparing a rapid or quick dissolve comestible unit is provided by mixing uncured shearform matrix and a controlled-release system, molding the mixture to form a unit dosage form, and curing the shearform matrix. Preferably, the shearform matrix includes a crystallization enhancer and/or a binding aid.

As used herein, controlled-release system can include a component selected from the group consisting of instantaneous release component(s), delayed release component(s), sustained release component(s), and combination thereof. Instantaneous release components can be provided by simply inclusion of raw active as an ingredient with the shearform matrix or can include a dispersion enhancer such as a surfactant, etc. A delayed release component is a component which has been treated by coating or otherwise to provide delayed bioavailability in the host. Such systems include, but are not limited to, polymeric coatings, biodegradable coatings, etc. Sustained release components are components which have been designed to provide a constant dosage release to the biosystem over a period of time. The present invention also includes combinations thereof.

The shearform matrix used to form dosage units in accordance with the invention can be made with flavors and/or sweeteners included in the feedstock used to make the matrix. Flavors can be chosen from natural and synthetic flavoring liquids. Sweeteners are those materials which provide sweetness to the matrix in addition to sweetness which is provided by the carrier material used to form the matrix, e.g., sucrose.

The mixture can be molded by being introduced in a unit dosage well and tamping the mixture therein. The tamped mixture is then cured by being subjected to environmental conditions of heat, moisture, and pressure which induce crystallization. For example, the unit can be cured by increasing the heat under substantially constant moisture condition. The heat can be increased by subjecting the tamped unit to microwave energy.

Another type of additive which can be used in the present invention is an effervescent disintegration agent. The term effervescent disintegration agent(s) includes compounds which evolve gas. The preferred effervescent agents evolve gas by means of chemical reactions which take place upon exposure of the effervescent disintegration agent to saliva in the mouth. The agent or agents can be included in several ways in the units of the present invention. First of all the agents can be incorporated in the matrix by mixing with the feedstock prior to flash flow processing. Alternatively, the entire effervescent agent can be mixed with the shearform matrix after it has been produced by flash flow techniques. As yet a third alternative, one part of the agent can be included in the feedstock which is flash flow processed while the other part of the agent can be incorporated after flash flow processing. In any event, the effervescent disintegration agent provides for controlled and rapid disintegration of the tablet when placed in the mouth and provides for a positive organoleptic sensation by the effervescent action in the mouth. The texture, speed and sensation of disintegration can especially be adapted for use by children in combination with taking one or more of the medicaments contemplated for use in the present invention.

"Tamping" is used herein to mean that the mixture is subjected to compression pressure of less than about 500 lbs. per sq. in. (psi), preferably less than 250 psi, and most preferably from about 20 to about 100 psi.

Another method of identifying the compression force required to mold uncured matrix in accordance with the present invention is by identifying the density resulting from tamping. The product of the present invention should be compressed in its uncured condition to a density of not greater than about 1.2, preferably not greater than about 0.8, and most preferably not greater than about 0.65. In one most preferred embodiment, the density of the finished product is between 0.25 and 0.40.

The product prepared in accordance with the method set forth above can dissolve in the mouth of the consumer in less than 10 seconds. Usually, well made product produced in accordance with this process will dissolve within less than 5 seconds, and, most preferably less than 3 seconds. The most highly dissoluble units have been described as literally "exploding" in the mouth.

In this first embodiment, the present invention also includes a composition for delivering a controlled-release system wherein the controlled-release system is incorporated in a molded saccharide-based crystalline structure. The composition also includes the saccharide-based structure which has a bi-dimensionally stabilized crystalline sugar. The sugar is produced by forming a sugar crystalline frame from an outer portion of an amorphous shearform sugar mass, and subsequently converting the remaining portion of the mass to a substantially completely crystalline structure. The product is preferably monodispersed and is also preferably microcrystalline. For definitions relating to monodispersed and microcrystalline as well as other definitions relating to the composition aspects of the present invention, reference is made to parent U.S. application Ser. No. 08/133, 669, filed Oct. 7, 1993, which is incorporated herein by reference. The shearform mass can also include an additive which is co-crystallized in a crystalline product. The amorphous shearform mass is substantially rod-shaped, and has two dimensions lying in a cross-sectional plane of the rod. The single dimension extends along a linear axis of the rod. Preferably, the monodispersed structurally stabilized cross-section does not exceed 50 μm, and preferably does not exceed 15 μm.

Yet another manifestation of the first embodiment of the present invention is a method of administering an active ingredient to a human host. The method includes ingesting a quick dissolve comestible unit prepared by the method of the present invention, i.e., mixing uncured shearform matrix and an active ingredient, followed by molding a unit dosage and curing the shearform matrix in the unit dosage form. The next step requires the host to retain the quick dissolve unit in the oral cavity for a time sufficient to contact the unit with water while in the oral cavity. Finally, the human host introduces water to the oral cavity while the unit is retained therein to enhance dissolution of the dosage unit.

As a result of the process of the first embodiment described herein, a rapidly dissolving dosage unit can be manufactured on a continuous basis and even prepared for shipment to the consumer in a single manufacturing line. The product can be made to provide the stunning sensation of exploding in the oral cavity upon ingestion by the consumer.

In a second embodiment of the present invention a method of preparing a comestible unit which quickly disperses in the mouth of the consumer is provided. The method includes initiating crystallization of shearform matrix either before or after combining the shearform matrix with a delivery system, as defined hereinabove, to form flowable, compactible micro-particulates. The combination, which includes at least partially crystallized shearform matrix, is then compacted to form the comestible unit.

Preferably, a crystallization/binding promoter is used to enhance the formation of flowable, compactible micro-particulates. The crystallization/binding promoter can be selected from the group consisting of an alcohol, such as ethanol, polyvinylpyrrolidone and a combination thereof. The promoter can also be a surface active agent. Surface active agents can be added to feedstock used to form the matrix. Alternatively, polydextrose can be used as a promoter by inclusion in the feedstock.

The shearform matrix can be prepared by flash flow processing feedstock which includes saccharide based material as a carrier component. Sucrose is a preferred carrier, and it can be combined with other saccharide based carrier components, such as dextrose, and sugar alcohols, such as sorbitol, mannitol, etc. The feedstock can also include a crystallization enhancer such as a surfactant, e.g., tweens, spans, etc.

In order to form the comestible unit, a medium compression force can be used without fear of disrupting the disintegratability of the unit. The compression force need not exceed ten (10) Strong Cobb Units ("SCU"), and preferably does not exceed medium compression forces of between six (6) and eight (8) SCU's. In some embodiments, a low compression force can also be used. In either event, tablets produced according to the invention can be made low density and easily disintegrated.

Another method of identifying the compression force required to mold uncured matrix in accordance with the present invention is by identifying the density resulting from compacting. The product of the present invention should be compacted to a density of not greater than about 1.2, and preferably not greater than about 0.8.

It has been found that the components of the delivery system are not "tied-up" with the components of the dosage unit. Consequently, active ingredients pharmaceuticals are made available to bio-systems for which they have been administered.

Another type of additive which can be used in the present invention is an effervescent disintegration agent. The term effervescent disintegration agent(s) includes compounds which evolve gas. The preferred effervescent agents evolve gas by means of chemical reactions which take place upon exposure of the effervescent disintegration agent to saliva in the mouth. The agent or agents can be included in several ways in the units of the present invention. First of all, the agents can be incorporated in the matrix by mixing with the feedstock prior to flash flow processing. Alternatively, the entire effervescent agent can be mixed with the shearform matrix after it has been produced by flash flow techniques. As yet a third possibility, one part of the agent can be included in the feedstock which is flash flow processed while the other part of the agent can be incorporated after flash flow processing. In any event, the effervescent disintegration agent provides for controlled and rapid disintegration of the tablet when placed in the mouth and provides for a positive organoleptic sensation by the effervescent action in the mouth. The texture, speed and sensation of disintegration can especially be adapted for use by children in combination with taking one or more of the medicaments contemplated for use in the present invention.

The present invention also includes a composition for delivering a controlled-release delivery system wherein the active ingredient is incorporated in a molded saccharide-based crystalline structure. The composition also includes the saccharide-based structure which has a bi-dimensionally stabilized crystalline sugar as defined hereinbefore.

Yet another manifestation of this embodiment is a method of administering an active ingredient to a human host. The method includes ingesting a quick dissolve comestible unit prepared by the method of the present invention. The next step requires the host to retain the quick dissolve unit in the oral cavity for a time sufficient to contact the unit with water while in the oral cavity. Finally, the human host introduces water to the oral cavity, while the unit is retained therein, to enhance dissolution of the dosage unit.

In all embodiments of the present invention, another feature includes reinforcing particles which inhibit destruction of components of the controlled-release system. Reinforcing particles have a size, shape, and hardness which are intended to withstand destructive pressure of an inadvertant bite by the consumer. For example, reinforcing particles can have a size which is up to 100 times larger that controlled-release components. The hardness is preferable greater than the hardness of the components of the controlled-release system. The shape is preferably one which does not detract from the texture and mouthfeel of the dosage unit during ingestion.

As a result of the present invention, a rapidly dispersible comestible unit can be manufactured for shipment and sales to consumers. The method of the present invention is such that the manufacturing can proceed on a continuous commercial scale. A unit can be formed which is durable and can withstand handling associated with packaging and distribution.

Moreover, the dispersability of the unit is perceived as nearly instantaneous. Consequently, the consumer does not experience disagreeable effects of unpleasant ingredients lingering in the oral cavity.

Furthermore, the component(s) of the controlled-release system can be made available to the host virtually without interference with ingredients therein.

These and other advantages of the present invention will be appreciated from the detailed description and examples which are set forth herein. The detailed description and the examples enhance the understanding of the invention, but are not intended to limit the scope of the invention.

DETAILED DESCRIPTION OF THE INVENTION

The present invention is a method of making comestible units which disintegrate quickly in the mouth of the consumer. The units produced in accordance with the present invention disintegrate nearly instantaneously. However, these units or tablets are capable of being manufactured so that they can be handled for packaging and distribution without deterioration of the integrity of the comestible units.

In the past, comestible units such as tablets have been made primarily by compressing feedstock under extremely high-pressure in order to provide the necessary hardness for handling required during packaging and distribution. Consequently, prior art tablets so produced are limited in that their high density reduces the capability of making them quickly disintegratable in the mouth. High density packing resulting from the high compression hinders the disintegration and wetting of the interior portion of the tablet. This aspect of the prior art has been improved by the technology disclosed in parent U.S. application Ser. No. 194,682, filed on Feb. 10, 1994.

As a result of the present invention, however, a significant step forward has been made in the art of preparing comestible units which disintegrate very quickly in the mouth and which can deliver a controlled-release system. In fact, tablets produced by the present invention disintegrate within seconds. The product is prepared by a unique combination of processing steps. The present invention also includes products which are produced by the new process.

The first step of the procedure of the first embodiment is to mix an uncured shearform matrix and a controlled-release system which includes an active ingredient, to prepare for molding a unit dosage. "Shearform matrix" in the present invention means a matrix produced by subjecting a feedstock which contains a carrier material to flash flow processing.

Flash flow processing can be accomplished several ways. Flash-heat and flash-shear are two processes which can be used. In the flash-heat process the feedstock material is heated sufficiently to create an internal flow condition which permits part of the feedstock to move at subparticle level with respect to the rest of the mass and exit openings provided in the perimeter of a spinning head. The centrifugal force created in the spinning head flings the flowing feedstock material outwardly from the head so that it reforms with a changed structure. The force necessary to separate and discharge flowable feedstock is centrifugal force which is produced by the spinning head.

One preferred apparatus for implementing a flash heat process is a "cotton candy" fabricating type of machine. The spinning machine used to achieve a flash-heat condition is a cotton candy machine such as the Econo-Floss Model 3017 manufactured by Gold Medal Products Company of Cincinnati, Ohio. Any other apparatus or physical process which provides similar forces and temperature gradient conditions can also be used.

In the flash-shear process, a shearform matrix is formed by raising the temperature in the feedstock material which includes a non-solubilized carrier, such as a saccharide-based material until the carrier undergoes internal flow upon application of a fluid shear force. The feedstock is advanced and ejected while in internal flow condition, and subjected to disruptive fluid shear force to form multiple parts or masses which have a morphology different from that of the original feedstock.

The multiple masses are cooled substantially immediately after contact with the fluid shear force and are permitted to continue in a free-flow condition until solidified.

The flash shear process can be carried out in an apparatus which has means for increasing the temperature of a non-solubilized feedstock and means for simultaneously advancing it for ejection. A multiple heating zone twin screw extruder can be used for increasing the temperature of the non-solubilized feedstock. A second element of the apparatus is an ejector which provides the feedstock in a condition for shearing. The ejector is in fluid communication with the means for increasing the temperature and is arranged at a point to receive the feedstock while it is in internal flow condition. The ejector is preferably a nozzle which provides high pressure ejection of the feedstock material. See co-pending commonly-owned U.S. patent application Ser. No. 965,804 filed Oct. 23, 1992 entitled "Process For Making Shearform Matrix," which is incorporated herein by reference.

The feedstock for producing shearform matrix includes a carrier material. The carrier material can be selected from material which is capable of undergoing both physical and/or chemical changes associated with flash-flow processing. Materials useful as matrices may be chosen from those carbohydrates which are capable of forming free-form agglomerates upon being processed.

Preferred materials useful as matrices may be chosen from such classes as "sugars". "Sugars" are those substances which are based on simple crystalline mono and di-saccharide structures, i.e., based on $C_5$ and $C_6$ sugar structures. "Sugars" include sucrose, fructose, lactose, maltose, and sugar alcohols such as sorbitol, mannitol, maltitol, etc. The preferred choice of sugar in the present invention is sucrose.

Preferred combinations of sugars includes sugars as used herein in combination with other mono-, di-, tri-, and polysaccharides up to 50% of the total amount, preferably up to 30% and most preferably up to 20%.

A shearform product is used in the technique of the present invention to obtain the new sugar product. A shearform sugar product is a substantially amorphous sugar which results from subjecting sugar to heat and shear sufficient to transform crystalline (usually granulated) sugar to amorphous sugar without the use of a solution. Thus, in the sense of the present invention, a shearform sugar product is characterized as a sugar product resulting from a non-solubilized sugar. It is the starting material for forming the unique crystalline product of the present invention.

Other carrier materials can be used, but preferably in combination with sugar—not as a total replacement.

Maltodextrins are an example of other carrier materials. Maltodextrins include those mixtures of carbohydrates resulting from hydrolysis of a saccharide feedstock which are described as solids having a DE of up to and including 65.

The feedstock can also include maltooligosaccharides produced by selective hydrolysis of cornstarch followed by removal of high and low molecular weight compounds. The general description of maltooligosaccharides as contemplated herein is set forth in co-pending U.S. application Ser. No. 07/847,595 filed Mar. 5, 1992.

Polydextrose is also contemplated for use as a carrier. Polydextrose is a non-sucrose, essentially non-nutritive carbohydrate substitute. It can be prepared through polymerization of glucose in the presence of polycarboxylic acid catalyst and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of co-pending, U.S. application Ser. No. 07/881,612 filed May 12, 1992.

As previously mentioned, each of the carriers are used primarily in combination with sugars, and not as a total replacement.

Other materials which can be incorporated into the feedstock to enhance the shearform matrix include flavors and sweeteners (other thorn the carrier itself).

Flavors may be chosein from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral, i.e., alphacitral (lemon, lime), neral, i.e., beta-citral (lemon, lime) decanal (orange, lemon), aldehyde C-8 (citrus fruits), aldehyde C-9 (citrus fruits), adlehyde C-12 (citrus fruits), tolyl aldehyde (cherry, almond), 2,6-dimethyloctanal (green fruit), and 2-dodecenal (citrus, mandarin), mixtures thereof and the like.

The sweeteners may be chosen from the following non-limiting list: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one- 2,2-dioxide, particularly the potassium salt (acesulfame-K), and sodium and calcium salts thereof. Other sweeteners may also be used.

Other ingredients can also be used in the present invention either during the mixing stage, during the agglomeration stage, or after the agglomeration stage. Such ingredients are ingredients which are useful in tabletting such as glidants which adhere to cohesive material and enhance flow properties. Flow property is enhanced by reducing interparticle friction which otherwise exists. Glidants which can be used includes starch, talc, magnesium and calcium stearate, zinc stearate, dibasic calcium phosphate, magnesium carbonate, magnesium oxide, calcium silicate, and silica arogels.

Also color additives can be used in preparing tablets. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Yet a further embodiment of the present invention includes the use of an effervescent disintegration agent. Its action can aid in the masking of objectionable taste of active ingredients such as vitamins, medicines and/or minerals, etc. It is generally believed that the positive organoleptic sensation achieved by the effervescent action in the mouth, the texture, speed and sensation of disintegration aids in masking undesirable flavor notes in the mouth.

In preferred embodiments of the present invention, the effervescent disintegration agent may include at least one acid selected from the group consisting of citric acid, tartaric acid, malic acid, fumaric acid, adipic acid, succinic acid, acid anhydrides and acid salts and mixtures thereof, and at least one base selected from the group consisting of carbonate salts, bicarbonate salts and mixtures thereof.

The term effervescent refers to those agents which evolve gas, and the bubble or gas generating the action is most often the result of the reaction of a soluble acid source and an alkali metal carbonate or carbonate source. The reaction of these two general classes of compounds produces carbon dioxide gas upon contact with water included in saliva. Carbonate sources include dry solid carbonate and bicarbonate salts such as sodium bicarbonate, sodium carbonate, potassium bicarbonate and potassium carbonate, magnesium carbonate and sodium sesequicarbonate, sodium glycine carbonate, L-lysine carbonate, arginine carbonate and amorphous calcium carbonate. While the food acids can be those indicated above, acid anhydrides of the above-described acids may also be used. Acid salts may include sodium, dihydrogen phosphate, disodium dihydrogen pyrophosphate, acid citrate salts and sodium acid sulfite. Other source of effervescence can be included and the present invention is not limited to those specifically set forth herein.

Also as previously mentioned, the ingredients of the effervescent agent can be included in one of at least three different ways. The first method includes incorporating the entire effervescent agent in the feedstock which is used to form the shearform product. The second manner of incorporating an effervescent disintegrating agent is to include the entire agent as an additive which is mixed with shearform matrix after it is formed. The third method contemplates incorporating one portion of the disintegrating agent in the shearform matrix and another portion of the disintegrating agent as an additive after formation of the shearform matrix material. The artisan will determine the best way to preserve the agent for its disintegrative and effervescent properties upon ingestion by the host.

The shearform matrix used in the inventive process must be uncured before it is molded. "Uncured" means amorphous or having a degree of amorphousness which enables the formation of a dosage unit upon curing. "Curing" means transforming the matrix from amorphous to crystalline while being sufficiently bound to produce a stable structure.

Curing can be enhanced by crystallization modifiers. Crystallization modifiers can be added to the feedstock before flash flow processing, such modifiers include, but are not limited to, surfactants (Spans™ and Tweens™), dextrose, polyethylene glycol (PEG), polypropylene glycol (PPG), etc. These modifiers generally provide controlled acceleration of crystallization while the matrix is bound.

Crystallization modifiers enhance the formation of a crystalline frame and the conversion of the remaining mass. Enhancement as used with respect to the process of the present invention principally means acceleration of the process. Enhancement also includes contribution to the strength of the crystalline structure, and predictability of results. Other benefits such as reduced-size product also is achieved by use of crystallization modifiers.

Crystallization modifiers, which are preferably added to sugars before being processed to amorphous shearform mass (or can be coated on the sugar), are used to affect the rate of crystallization. Water itself is a crystallization modifier, and is preferably included in the amorphous shearform sugar mass in an amount of between about 0.5% to about 2.0%. Non-saccharide hydrophilic organic materials (NSHMs) are also used as crystallization modifiers. Even though some NSHMs are surfactants, other materials can be used. Materials found to be most effective have a hydrophilic to lipid balance (HLB) of 6 or greater, i.e., they have the same degree of hydrophilicity as surfactants characterized by degree of HLB. Such materials include, but are not limited to anionic, cationic, zwitterionic surfactants as well as neutral materials which have an HLB of six (6) or greater. Preferred NSHMs are hydrophilic materials having polyethylene oxide linkages. Also, the preferred NSHM's have a molecular weight of at least 200 and preferably at least 400.

Lecithin is one surface active agent for use in the present invention. Lecithin can be included in the feedstock in an amount of from about 0.25 to about 2.00% by weight. Other surface active agents include, but are not limited to, the Spans™ and Tweens™ which are commercially available from ICI Americas Inc. Carbowax™ is yet another crystallization modifier which is very useful in the present invention. Preferably, Tweens™ or combinations of surface active agents are used to achieve the desired HLB.

By use of a surfactant the process and product of the present invention can be reproduced with a high degree of predictability. As additional crystallization modifiers which enhance the procedure and product of the present invention are identified, Applicants intend to include all such additional crystallization modifiers within the scope of the invention claimed herein.

The process of the present invention requires mixing an additive with the uncured shearform matrix. When the shearform matrix is in the form of a floss, it is preferably chopped first to reduce the volume of the product without compressing it. The additive can be any ingredient or ingredients needed to supply the dosage unit with the required characteristics. The primary ingredients are medicinal substances.

In a second embodiment of the present invention, the controlled-delivery system is combined before or after initiating crystallization.

"Initiating crystallization" in the present invention means to induce crystallization. Shearform matrix used in the present invention contains a substantial amount of amorphous sugar. Crystallization can be initiated several ways. For example, crystallization promoters can be included in the feedstock used to make the shearform matrix. Crystallization promoters include surface active agents such as Tweens™, Spans™, and polydextrose, and mixtures thereof. Crystallization can also be initiated by adding a crystallization agent to the matrix before or after combining with an additive. Therefore, initiating crystallization in the present invention can occur before or after combining with the additive.

"Combining" an additive with shearform matrix to form flowable, compactible micro-particulates means to add and mix an additive before or after initiating crystallization to form a medium which consists of micro-particulates. Micro-particulates are discreet entities which appear to "roll" readily or "flow" in response to force of gravity and/or agitation. On a macroscopic scale micro-particulates appear as a flowable mass or medium. Consequently, the medium can be easily used in tabletting machinery without clogging and/or creation of undue dust in the ambient atmosphere.

The shearform matrix of the present invention is retrieved from processing, and generally "chopped" before combining with the additive. The additive can be any ingredient or ingredients needed to supply the comestible unit with the required characteristics. Preferably, the primary ingredient of the additive is one or more medicinal substances.

Medicinal substances which can be used in the present invention are varied. The medicinal substances can be encapsulated for controlled release. A non-limiting list of medicinal substances is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, antiuricemic drugs and mixtures thereof.

Especially preferred active ingredients contemplated for use in the present invention are antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include aspirin, acetaminophen, and acetaminophen plus caffeine.

Other preferred drugs for other preferred active ingredients for use in the present invention include antadiarrheals such as immodium AD, antihistamines, antitussives, decongestants, vitamins, and breath fresheners. Also contemplated for use herein are anxiolytics such as Xanax; antipsychotics such as clozaril and Haldol; non-steroidal anti-inflammatories (NSAID's) such as Voltaten and Lodine; antihistamines such as Seldane, Hismanal, Relafen, and Tavist; antiemetics such as Kytril and Cesamet; bronchodilators such as Bentolin, Proventil; antidepressants such as Prozac, Zoloft, and Paxil; antimigraines such as Imigran, ACE-inhibitors such as Vasotec, Capoten and Zestril; Anti-Alzheimers agents, such as Nicergoline; and $Ca^H$-Antagonists such as Procardia, Adalat, and Calan.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Other ingredients which may be included are fragrances, dyes, sweeteners both artificial and natural, and other additives.

For example, fillers may be used to increase the bulk of the tablet. Some of the commonly used fillers are calcium sulfate, both di- and tri basic, starch, calcium carbonate, microcrystalline cellulose, modified starches, lactose, sucrose, mannitol, and sorbitol.

Other ingredients includes binders which contributes to the ease of formation and general quality of the tablet. Binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Lubricants can also be used to aid in tamping and compacting. Lubricants can include, but are not limited to, the following: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

Furthermore, disintegrants can be used to enhance the dispersibility of the compressed tablet in an aqueous environment. The dispersants can include starch, alginic acid, guar gum, kaolin, bentonite, purified wood cellulose, sodium starch glycolate, isoamorphous silicate, and microcrystalline cellulose. In view of the highly dissoluble nature of the product of the present invention, there is little need for disintegrants.

Another ingredient useful in tabletting are glidants which adhere to the cohesive material in order to enhance flow properties by reducing interparticle friction. Glidants which can be used include starch, talc, magnesium and calcium stearate, zinc stearate, dibasic calcium phosphate, magnesium carbonate, magnesium oxide, calcium silicate, and silica aerogels.

Furthermore, dispersion enhancers can be used to enhance the breakability of the compressed tablet in an aqueous environment. The dispersants can include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants. In view of the ease with which the product of the present invention disintegrates, there is little need for disintegrants.

Color additives useful in preparing tablets include food, drug and cosmetics (FD&C) colors, drug and cosmetic (D&C) colors, or external drug and cosmetic (Ext. D&C) colors. These colors are dyes, their corresponding lakes, and certain natural and derived colorants. Lakes are dyes absorbed on aluminum hydroxide.

In a preferred embodiment, the present invention is particularly useful in preparing antacid tablets. Antacids are conveniently provided in chewable tablet form to provide a convenient method of delivering antacid to the consumer. The chewable form provides an advantage in that the tablet is broken up into granules during chewing and mixed with saliva before swallowing. This renders the tablet antacid formulation a suspension. One of the disadvantages of prior art antacid tablets is that the mass of ingredients residing in the mouth during and after chewing have objectional texture and taste. The present invention overcomes these disadvantages because the ingredients virtually explode into dissolution. The texture is also significantly enhanced and the residence time is substantially reduced.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

After the controlled-release system has been mixed with the uncured shearform matrix, the result of mixture must be "molded" as a unit dosage form.

"Molding" is used herein to mean associating uncured (i.e., uncrystallized) shearform matrix material closely enough to provide bridging between crystallized matrix material upon curing. Generally, this requires force sufficient to provide intimate contact of fibers prior to curing, followed by crystallizing to form a bound continuous crystalline structure throughout the tablet. Unlike conventional tabletting which relies primarily on compression to provide the structure, the present process utilizes the curing process to aid in forming the end product. Consequently, mild compression forces can be used to mold the product. In a preferred embodiment, the compression required to mold uncured matrix material is referred to as "tamping."

"Tamping" means compressing with force less than that required in compression tabletting, which is generally regarding as being on the order of thousands of pounds per square inch (psi). The maximum pressure used in the present invention is only 500 psi, but in most cases will never exceed about 250 psi, and, in the most preferred embodiments, not more than 80 psi (e.g., 40 psi to 80 psi). These lower pressures are called tamping.

Another method of measuring the compression force required to "mold" uncured matrix is by product density. The product of the present invention should be compressed in an uncured condition to a density of not greater than about 1.20, preferably not greater than 0.8, and, most preferably, not greater than 0.65.

Inasmuch as one method the present invention requires extremely low pressures for molding, it is possible to mold directly in plastic product wells which can be used as packaging for sales. Consequently, the present invention includes the concept of molding uncured matrix materials clearly in product wells such as plastic blister package depressions.

In the second embodiment, the present inventor requires compacting the combination resulting from "combining" the controllable release delivery system and the shearform matrix.

"Compacting" in the present invention means to press into a comestible unit, e.g., a tablet, at a pressure generally greater than about 500 psi, but not necessarily as great as normal tabletting pressure, which are on the order of magnitude of thousands of psi (i.e., at least about 1000 psi). In one preferred embodiment wherein polydextrose (especially, Poly Dex™ brand polydextrose provided by A. E. Stanley & Co.) has been included as a crystallization promoter, compaction pressure as low as 50 psi has been found to be effective. In all cases herein, the micro-particulate medium being compacted includes shearform matrix which has been at least partially crystallized.

The combination of shearform matrix and the additive must be provided as flavorable, compactible micro-particulates. The micro-particulates are agglomerates of a sort which include the ingredients of the mixture, but which are relatively low density. The "micro-particulates" of the present invention are capable of withstanding relatively high compaction force without experiencing an increase in density. The micro-particulates can then be compacted under relatively high compaction force to form a low density dosage unit having high structural integrity, strength and excellent appearance.

Micro-particulates are preferably formed by combining the mixture with a crystallization/binding promoter such as ethanol (preferably 200 proof), polyvinylpyrrolidone, a combination thereof, as well as other agents which enhance the formation of micro-particulates without increasing the density of the mixture.

The micro-particulates resulting from the above step can then be compacted, e.g, 6–8 SCUs (Strong Cobb Units), whereby a structurally strong tablet can be formed which has excellent appearance and can be handled without deterioration of the surface or structure.

After preparing shearform matrix and molding the uncured matrix, the product must be cured. Curing means binding and crystallizing the matrix material substantially simultaneously. Curing is performed by subjecting product to heat and moisture sufficient to provide controlled crystallization. Controlled crystallization occurs when points of contact of uncured matrix material become points of crystalline growth and crystallization of the material proceeds to provide crystalline structures. Binding occurs at the points of contact, and the simultaneous crystalline growth is such as to maintain structural integrity.

The "curing" process of the present invention involves a transformation from amorphous to crystalline state. The transformation must take place while the amorphous shearform matrix remains bound together.

Moreover, curing requires the transformation to take place without collapsing the structural integrity of the matrix in its "formed" condition. Since amorphous shearform product is hygroscopic, this transformation can be difficult. When points of contact between pieces of matrix can be made points of crystalline growth during curing, structural integrity is established and maintained. One way of promoting the occurrence of this phenomenon is to include crystallization enhancers, e.g., surfactants, any alcohol, polyethylene glycol, polypropylene glycol, etc. Without being bound by theory, it is believed control of the propagation of crystalline growth as outlined above is improved significantly by use of crystallization enhancers.

Prior to curing, the mixture of shearform matrix and active are maintained at temperature and humidity below the glass transition temperature of the shearform matrix material.

Conditions suitable for curing can include ambient conditions of heat and moisture or modified ambient conditions. For example, it has been found that curing can be conducted at a temperature of 0°–90° C. at a relative humidity of 25–90%. In one case, it has been found that curing will take place within 15 minutes at 40° C. and 85% r.h. In other cases, optimum temperature range has ben found to be at 20°–50° C. Microwave energy can be used to controlledly accelerate curing.

Generally, the crystallization is effected in an environment wherein the tabletted material cures to a water content of less than 5% by weight, and preferably less than 1% by weight based on the weight of the tablet. Thus, the curing environment, e.g., chamber or room, is maintained at a relative humidity which permits water pickup no greater than 5%, and preferably less than 1%.

It has been found that curing product in a package well results in shrinkage of the tablet from the walls of the well. This feature is particularly advantageous for purposes of manufacturing individual dosage units since molding and curing can be performed in the package used for commercial sales. Consequently, several transfer steps can be eliminated.

Products prepared in accordance with the present invention have been found to have densities of from about 0.20 gm/cc$^2$ to about 0.90 gm/cc$^2$, and some preferred embodiments have densities of from about 0.40 gm/cc$^2$ to about 0.65 gm/cc$^2$.

Another ingredient which can be included in the shearform matrix is a binding aid or agent. A binding agent is used to assist in the molding step and, in some cases, contributes to the dissolution capabilities of the finished product. Binding agents useful herein include low-glass-transition materials. Some agents found useful include, but are not limited to, sorbitol, mannitol, lactose, etc. The binding agents are flash flow processed with the carrier. Binding agents also aid in holding the matrix material in place for curing. In some cases portions of the binder becomes part of the matrix material.

In the second embodiment of the present invention, one method of measuring the results of the present invention is the ability to make a low density product. The micro-particulates are capable of being subjected to high-pressure without reducing the density of the resulting product. Accordingly, the product prepared in accordance with the present invention even after high-pressure-compaction will still remain below 1.2 grams per cubic centimeter (gr./cc), and preferably below 0.8 gr./cc.

The pressure required to prepare tablets in accordance with the present invention exceed those generally required in the first embodiment described herein, but are less than those previously required with normal tabletting procedures (albeit some embodiments require no greater compaction pressure than that set forth in U.S. application Ser. No. 08/259,258). As a result of the increase pressure which can be used to form tablets in accordance with the present invention, the strength of the product is increased, and the hardness of the surface is also increased. This results in a confection dosage unit which is able to be handled manually and machine processed without degradation of the surface or structural integrity.

Micro-particulates retain their individual integrity and lines of disintegration are provided throughout the resulting unit. Moreover, since the mass can be subjected to relatively high-pressure-compaction, the surface of the resulting dosage unit is smooth, and the strength of the tablet is relatively high. Therefore, the resulting units can be easily handled without deterioration of the surface appearance or destruction of the comestible units.

In the formation of the micro-particulates the material preferably contains up to 5% water, and most preferably up to 1% water. The water can be provided by water contained in the ingredients such as that carried in the sugars or binders. Water can also be provided in small amounts in the alcohol, such as in 200 proof alcohol which absorbs moisture rapidly and generally contains small amounts of moisture, e.g., up to 1% by weight. The additional moisture can be provided by ambient surroundings such as the humidity in the air.

The present invention has been found to be well suited for preparation of antacid tablets and tablets in which antacids are used as an ingredient to ameliorate the acid conditions in the body in order to assist drugs which do not tolerate acidic conditions. In the case of antacids themselves, the instantaneous dispersion of the tablet in the mouth prevents the residual chalky taste of a conventional antacid tablet. In the case of ingredients which do not tolerate acidic conditions, it is desirable to include the antacids plus the "acid-sensitive" pharmaceutical in a dosage unit prepared according to the invention. For example, didanosine is an antiviral agent which does not tolerate an acidic environment well. Consequently, the use of didanosine in combination with an antacid such as calcium carbonate in the same drug delivery system is an ideal method of introducing the drug to the body. The present invention includes the combination of an "acid-sensitive" ingredient and an antacid in a dosage unit.

The shearform matrix material used in the following examples is an amorphous sugar. Amorphous sugar as used herein means a sugar stock which contains a high percentage of amorphism, i.e., greater than 50% by weight, and preferably greater than 70% by weight of the sugar stock is amorphous.

EXAMPLE

A controlled release system was prepared in accordance with the present invention by preparing a shearform matrix using a combination of 49.75% sucrose, 0.025% Tween 80 as a surfactant, 40% Cantab™ (a crystalline form of a high D.E., Dextrose Equivalent, Corn Syrup product of Penwest Foods Co., Cedar Rapids, Iowa), and 10% D-Xylose. The shearform matrix was collected and comminuted to a small consistent size and stored in an airtight container and subsequently formulated for tabletting.

The tablet formulation was prepared with 60% floss as set forth above, 37% Contact brand cold medicine, 0.55% Aspartame, 0.5% coloring, 1% Comprital HD5 (a Glycerol Polyethylene Glycol Behenate product of Gattefossé Westwood, N.J.), and 0.50% Syloid 244 FP flow agent. The combination was blended in a manner which ensured the drug was substantially homogenously mixed with the other ingredients.

The combination was subsequently weighed into 0.7 gram samples and loaded into a press and tabletted by tamping at a 40 pound per square inch pressure for approximately five seconds.

The resulting tablets had a very uniform and attractive surface, and maintained good physical integrity. The tablets were sealed in a blister pack. Tablets crystallized in the packaging over a 24 hour period.

The tablets produced by the process set forth above were rapidly dispersable in the oral cavity. The drug was also rapidly dispersed and it is believed that the process could be easily adapted to existing commercial drug tabletting facilities.

Thus, while there had been described what are presently believed to be the preferred embodiments of the present invention, other and further modification and changes can be made thereto without departing from the true spirit of the invention. It is intended to include all further and other modifications and changes which come within the true scope of the invention as set forth in the claims.

What is claimed is:

1. A method of preparing quick dissolve comestible units having a controlled-release system comprising:

subjecting a feedstock which contains a carrier material to flash-flow processing to provide uncured shearform matrix;

chopping said uncured shearform matrix;

mixing said chopped uncured shearform matrix and a controlled-release system comprising a composition for making an active ingredient available to a host biological system with components selected from the group consisting of an instantaneous release component, a delayed released component, a sustained release component, and combinations thereof;

molding the mixture of uncured shearform matrix and controlled-release system resulting from the previous step to provide a unit dosage form which has bridging between crystallized matrix material upon curing; and curing said shearform matrix to produce a stable structure.

2. The method of preparing quick dissolve comestible units in accordance with claim 1, wherein said shearform matrix further comprises a crystallization enhancer.

3. The method of preparing quick dissolve comestible units in accordance with claim 1, wherein said shearform matrix further comprises a binding agent.

4. The method of preparing quick dissolve comestible units in accordance with claim 1, wherein said molding comprises introducing the mix resulting from the mixing step to a unit dosage well and tamping said mix.

5. The method of preparing quick dissolve comestible units in accordance with claim 1, wherein curing comprises subjecting to ambient conditions of heat, moisture, and pressure which induce crystallization.

6. The method of preparing quick dissolve comestible units in accordance with claim 5, wherein said heat is increased under substantially constant moisture conditions.

7. The method of preparing quick dissolve comestible units in accordance with claim 6, wherein said heat is increased by subjecting to microwave energy.

8. The method of preparing quick dissolve comestible units in accordance with claim 1, wherein said controlled release system includes an active ingredient selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, anti-thrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

9. The method of preparing quick dissolve comestible units in accordance with claim 4, wherein said tamping is performed at a pressure of less than about 500 psi.

10. The method of preparing quick dissolve comestible units in accordance with claim 9, wherein said pressure is less than about 250 psi.

11. The method of preparing quick dissolve comestible units in accordance with claim 10, wherein said pressure is from about 20 psi to about 100 psi.

\* \* \* \* \*

UNITED STATES PATENT AND TRADEMARK OFFICE
CERTIFICATE OF CORRECTION

PATENT NO. : 5,567,439
DATED : October 22, 1996
INVENTOR(S) : Myers, et al.

It is certified that error appears in the above-indentified patent and that said Letters Patent is hereby corrected as shown below:

IN THE TITLE PAGE:

Title [54], Line 2 and in column 1, lines 1-2 delete title "Delivery of Controlled-Release Systems(s)", and insert therefor--Delivery of Controlled-Release System(s)--.

Signed and Sealed this

Fourth Day of March, 1997

Attest:

BRUCE LEHMAN

*Attesting Officer*   *Commissioner of Patents and Trademarks*